United States Patent
Smith et al.

(10) Patent No.: US 11,583,660 B2
(45) Date of Patent: Feb. 21, 2023

(54) FEMALE URETHRAL CATHETERIZATION ASSIST DEVICE

(71) Applicants: Susan Smith, Lizella, GA (US); Carl Hofstadter, Jr., Macon, GA (US)

(72) Inventors: Susan Smith, Lizella, GA (US); Carl Hofstadter, Jr., Macon, GA (US)

(*) Notice: Subject to any disclaimer, the term of this patent is extended or adjusted under 35 U.S.C. 154(b) by 342 days.

(21) Appl. No.: 15/782,237

(22) Filed: Oct. 12, 2017

(65) Prior Publication Data
US 2018/0099118 A1 Apr. 12, 2018

Related U.S. Application Data

(60) Provisional application No. 62/407,039, filed on Oct. 12, 2016.

(51) Int. Cl.
*A61M 25/01* (2006.01)
*A61B 17/02* (2006.01)
*A61B 17/44* (2006.01)

(52) U.S. Cl.
CPC ......... *A61M 25/01* (2013.01); *A61B 17/0206* (2013.01); *A61B 17/44* (2013.01); *A61M 2210/1092* (2013.01)

(58) Field of Classification Search
CPC .......... A61M 25/01; A61M 2210/1092; A61B 17/0206; A61B 17/44; A61B 17/2812; A61B 17/4241; A61B 18/085; A61B 18/1445
See application file for complete search history.

(56) References Cited

U.S. PATENT DOCUMENTS

| | | | | |
|---|---|---|---|---|
| 2,583,892 A | * | 1/1952 | Shellhouse | A61B 17/42 606/167 |
| 3,885,563 A | * | 5/1975 | Johnson | A61F 13/2051 604/14 |
| 4,502,485 A | | 3/1985 | Burgin | |
| 4,559,944 A | | 12/1985 | Jaeger | |
| D319,877 S | * | 9/1991 | O'Neal-Cox | D24/143 |
| 5,569,300 A | | 10/1996 | Redmon | |
| 5,849,017 A | | 12/1998 | Reynolds et al. | |
| 6,302,842 B1 | * | 10/2001 | Auerbach | A61B 17/0206 600/219 |
| 7,083,613 B2 | | 8/2006 | Treat | |
| 7,104,980 B1 | * | 9/2006 | Laherty | A61M 25/01 604/528 |
| 2003/0055319 A1 | * | 3/2003 | Chang | A61B 17/0206 600/210 |
| 2005/0027170 A1 | * | 2/2005 | Nohara | A61B 17/0206 600/219 |

(Continued)

*Primary Examiner* — Philip R Wiest
*Assistant Examiner* — Alessandro R Del Priore
(74) *Attorney, Agent, or Firm* — Boudwin Intellectual Property; Daniel Boudwin

(57) ABSTRACT

A female urethral catheterization assist device and method of use. The female urethral catheterization assist device includes a pair of lateral arms pivotally connected at a middle point that enables a user to selectively open and close the lateral arms. A handle is positioned at one end of each lateral arm and a paddle is disposed at an opposing end. The paddles extend in the same direction and form an interior lateral side. Each paddle is adapted to engage with a labia minora and majora, to allow for the insertion of a female urethral catheter.

1 Claim, 4 Drawing Sheets

(56) References Cited

U.S. PATENT DOCUMENTS

| | | | | |
|---|---|---|---|---|
| 2005/0267336 A1* | 12/2005 | Bertolero | .......... | A61M 25/1027 600/219 |
| 2006/0100607 A1* | 5/2006 | Brown | ............... | A61M 25/0111 604/544 |
| 2010/0317928 A1* | 12/2010 | Subramaniam | .... | A61B 17/0206 600/245 |
| 2012/0296172 A1* | 11/2012 | Raven, III | ......... | A61B 17/0206 600/231 |
| 2017/0311942 A1* | 11/2017 | Daavettila | .......... | A61B 17/0293 |

* cited by examiner

FEMALE URETHRAL CATHETERIZATION ASSIST DEVICE

CROSS REFERENCE TO RELATED APPLICATION

This application claims the benefit of U.S. Provisional Application No. 62/407,039 filed on Oct. 12, 2016. The above identified patent application is herein incorporated by reference in its entirety to provide continuity of disclosure.

BACKGROUND OF THE INVENTION

Field of the Invention

The present invention relates to a device and method of inserting a female urethral catheter. More specifically, the present invention provides a female urethral catheterization assisting device having a pair of opposing lateral arms pivotally connected so as to allow for the selective opening and closing thereof. The lateral arms each include a paddle disposed at a distal end that extends from a first side that engages with a labia minora and majora of a female patient and exposes the urinary meatus.

Devices have been disclosed in the known art that relate to female urethral catheter devices. These include devices that have been patented and published in patent application publications. However, these devices in the known art have several known drawbacks. For example, these known devices fail to provide a female urethral catheterization assisting device that provides a full and clear view of the urethral opening for ease of catheterization by clinical or non-clinical persons.

In light of the devices disclosed in the known art, it is submitted that the present invention substantially diverges in design elements from the devices in the known art and consequently it is clear that there is a need in the art for an improvement to existing female urethral catheter devices. In this regard, the instant invention substantially fulfills these needs.

SUMMARY OF THE INVENTION

In view of the foregoing disadvantages inherent in the known types of female urethral catheter devices now present in the art, the present invention provides a new female urethral catheter assist device wherein the same can be utilized for providing convenience for the user when inserting a female urethral catheter. The female urethral catheter comprises a pair of interconnected lateral arms, wherein each lateral arm includes a paddle disposed on one end that are configured to engage a labia minor and labia majora so as to provide a full and clear view of the urethral opening.

It is therefore an object of the present invention to provide a new and improved female urethral catheter assist device. The female urethral catheter assist device includes a pivot that fixes the angle of the pair of lateral arms at an optimal angle.

It is another object of the present invention to provide a female urethral catheter assist device that locks in an open configuration to expose the urinary meatus of a patient for insertion of a female urethral catheter.

Another object of the present invention is to provide a female urethral catheter assist device that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
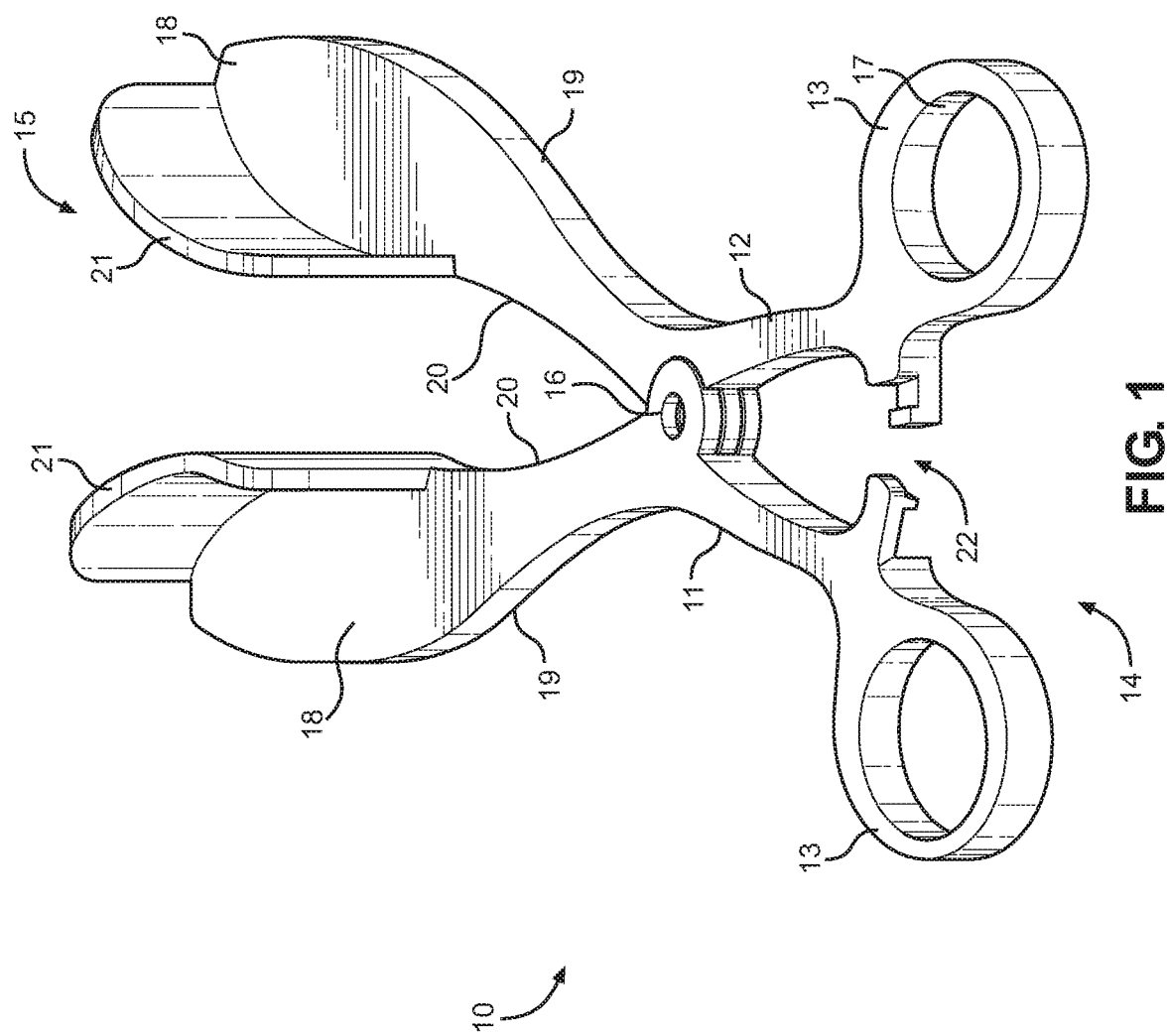
FIG. 1 shows a perspective view of the female urethral catheter assist device.

Reference is made herein to the attached drawings. Like reference numerals are used throughout the drawings to depict like or similar elements of the female urethral catheter assist device. For the purposes of presenting a brief and clear description of the present invention, the preferred embodiment will be discussed as used for assisting with the insertion of a female urethral catheter. The figures are intended for representative purposes only and should not be considered to be limiting in any respect.

Figure 2:
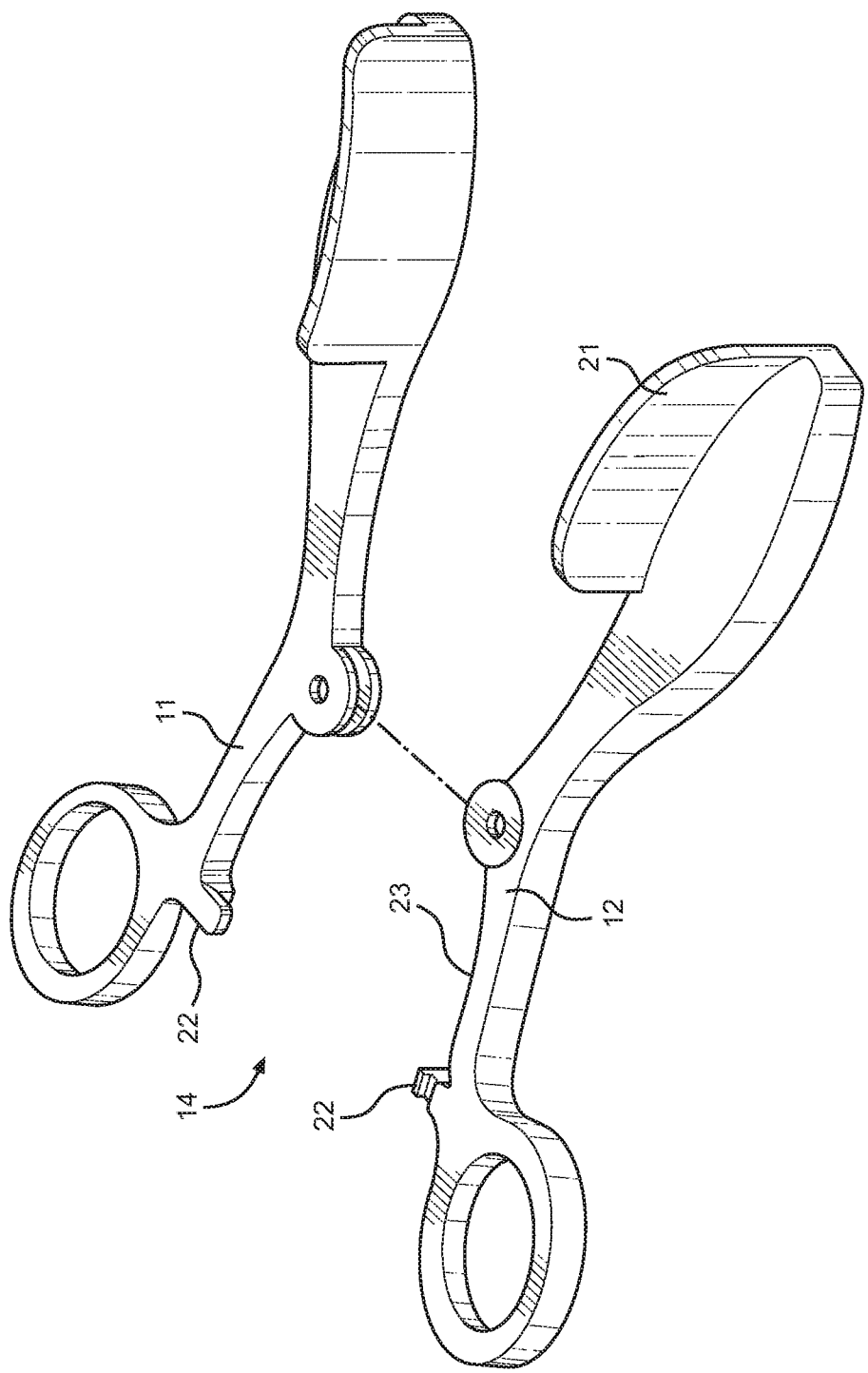
FIG. 2 shows an exploded view of the female urethral catheter assist device

Referring specifically to FIGS. 1 and 2, there is shown a perspective view and an exploded view of the female urethral catheter assist device, respectively. The female urethral catheter assist device 10 provide a medical device that engages with a labia minora and majora to expose the urinary meatus of a patient, and therefore allow for easy insertion of a female urethral catheter therein. The female urethral catheter assist device 10 comprises a pair of a lateral arms comprising a first lateral arm 11 and a second lateral arm 12 interconnected via a pivot 16. Each lateral arm 11, 12 includes a handle 13 at a first end 14. The pivot 16 rotatably connects the lateral arms 11, 12 intermediate the first end 14 and a second end 15, such that movement of the handles 13 towards each other causes movement of the second ends 15 of the lateral arms 11, 12 away from each other. In the shown embodiments, the pivot 16 includes a series of apertures configured to align and receive a pin therethrough. Thus, the lateral arms 11, 12 are rotatable about the pivot 16. However, in alternative embodiments, the pivot 16 may comprise other pivoting and hinged members.

In the shown embodiments, the handles 13 comprise a centrally disposed aperture 17 configured to receive a finger therethrough. The handles 13 are integrally formed with each lateral arm 11, 12 and extend therethrough, along an axis parallel the pivot 16. A fastener 22 is disposed towards the first end 14 of each lateral arm 11, 12 and is configured to couple the handles 13 of the lateral arms 11, 12 to each other. In the shown embodiment, the fastener 22 is disposed along an internal lateral side 23 of the proximal end 14 and is configured to selectively couple the first lateral arm 11 to the second lateral arm 12, forming an open configuration.

The open configuration is formed when the distal end 15 of the lateral arms 11, 12 are rotated away from each other. In the shown embodiments, the fastener 22 comprises a transverse bar having a latch configured to couple with a mating fastener 22 disposed on the opposing lateral arm. In alternative embodiments, the fastener 22 comprises any member with a locking mechanism configured to selectively fix the angle formed between the ends of the lateral arms 11, 12.

The distal end 15 of each lateral arm 11, 12 comprises a first side 18 positioned between a pair of curved lateral sides 19, 20. The second end 15 of each blade 11, 12 includes a bulbous distal end, wherein each of the lateral sides 19, 20 are curved such that each lateral side 19, 20 tapers inwardly toward the pivot 16. A paddle 21 extends perpendicular from the first side 18 and from an interior lateral side 20 of the curved lateral sides 19, 20. In the shown embodiment, the paddles 21 form a flush, continuous surface with the interior lateral side 20. However, in alternative embodiments, the paddles 21 may be offset from the interior lateral sides 20. The paddles 21 are configured to engage and spread a labia minora and majora to expose a urinary meatus of a patient for insertion of a female urethral catheter.

Figure 3A:
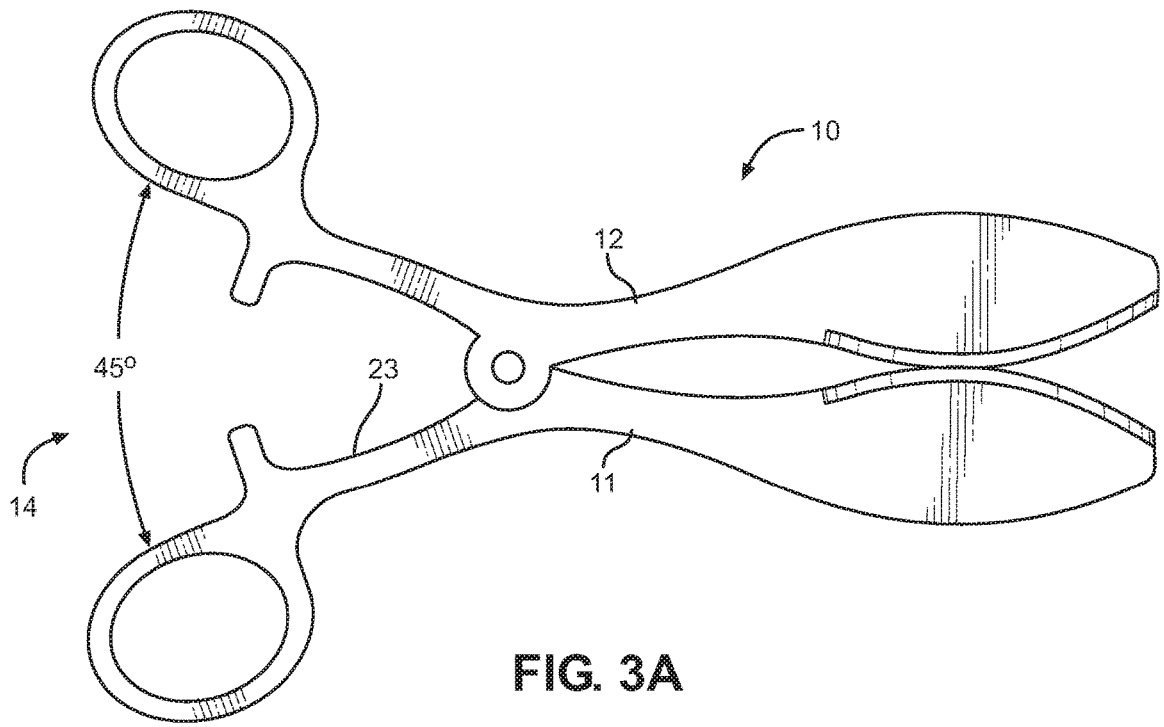
FIG. 3A shows an overhead view of the female urethral catheter assist device in a closed configuration.
Figure 3B:
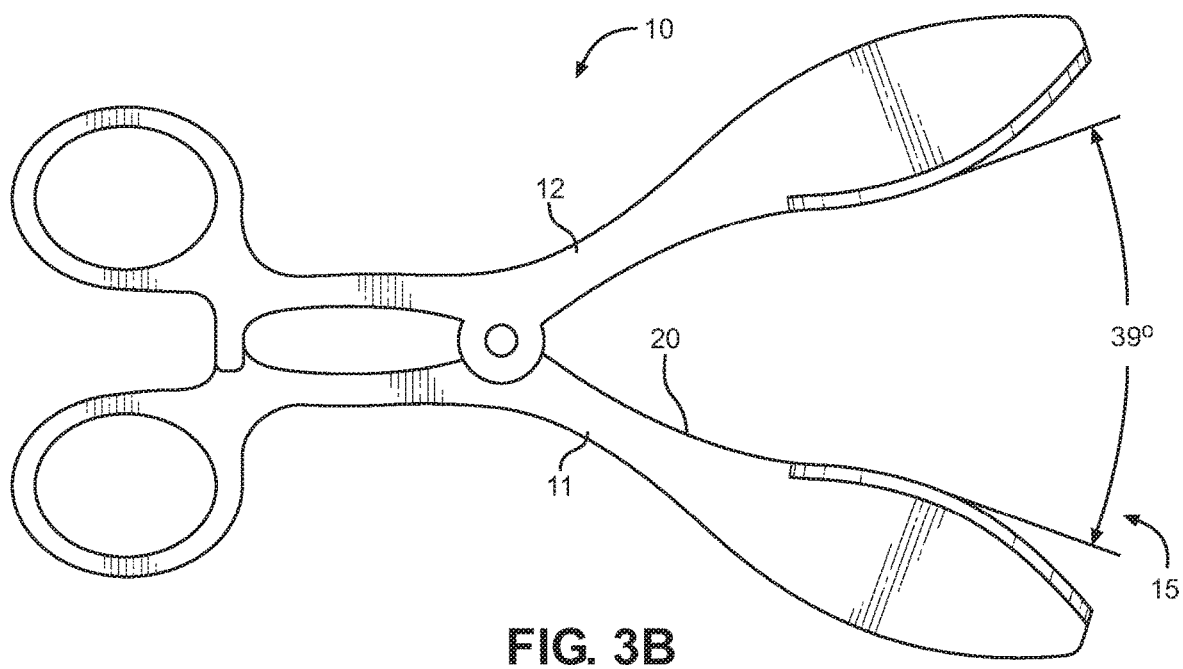
FIG. 3B shows an overhead view of the female urethral catheter assist device in an open configuration.

Referring specifically to FIGS. 3A and 3B, there is shown an overhead view of the female urethral catheter assist device in the closed configuration and an overhead view of the female urethral catheter assist device in the open configuration, respectively. In the shown embodiments, the female urethral catheter assist device 10 is configured to open and close between a range of angles when measured between the interior lateral side of the proximal end 23 and the interior lateral side of the distal end 20. The open configuration is formed when the distal ends 15 of the lateral arms 11, 12 are rotated away from each other. In one embodiment, the angle formed therebetween is thirty-nine degrees. However, in alternative embodiments, the angle may be in a range may be more than five degrees. The closed configuration is formed when the proximal ends 14 of the lateral arms 11, 12 are rotated away from each other. In one embodiment, the angle formed therebetween is forty-five degrees. However, in alternative embodiments, the angle may be more than five degrees.

Figure 4:
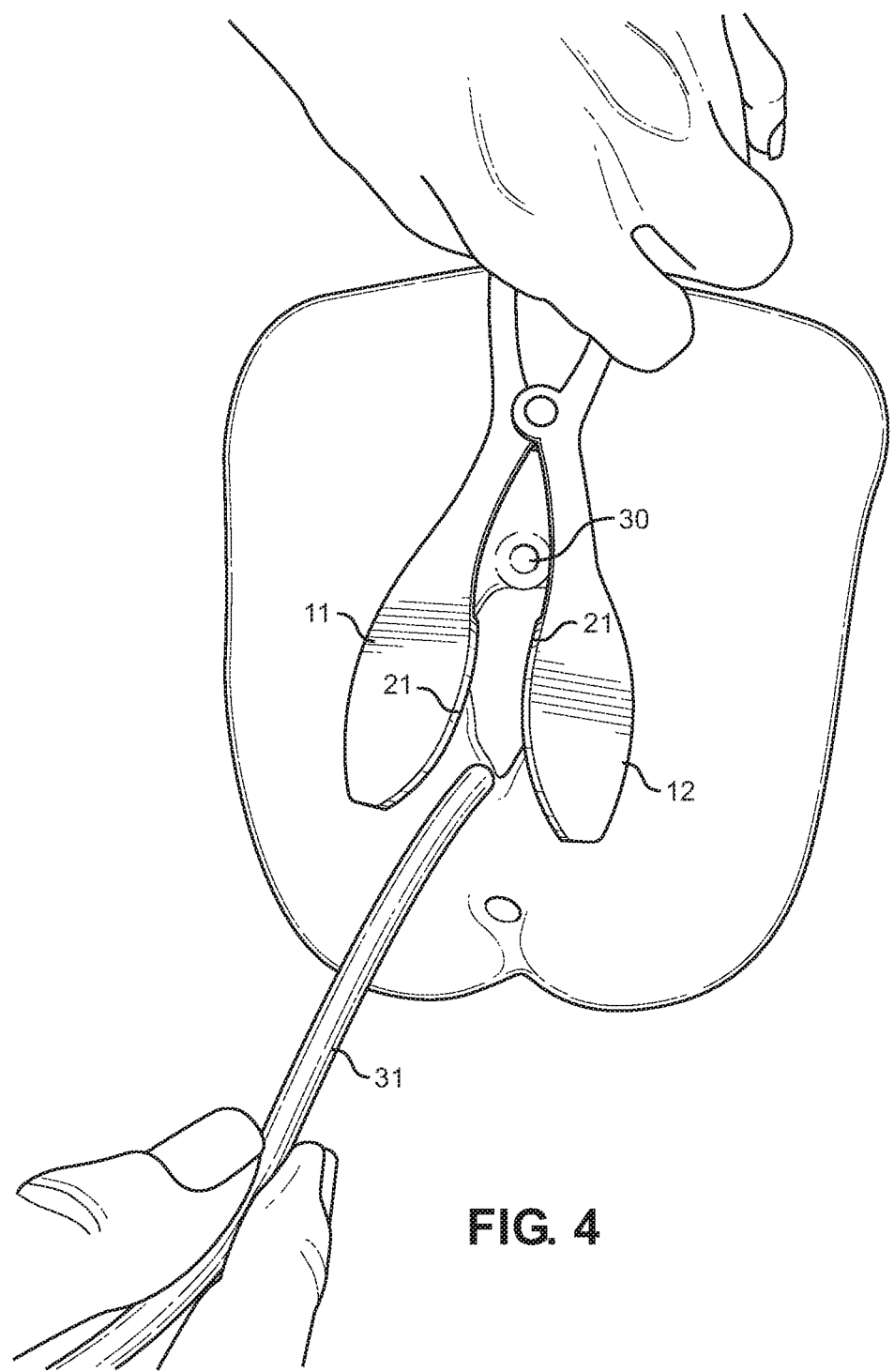
FIG. 4 shows an in-use view of the first embodiment of the female urethral catheter assist device.

Referring specifically to FIG. 4, there is shown an in-use view of the first embodiment of the female urethral catheter assist device. A method of inserting a female urethral catheter comprises: inserting a paddle 21 of each of the lateral arms '11, 12 of the female urethral catheterization assist device in a closed configuration to engage with a labia minora and majora, opening the female urethral catheterization assist device to an open configuration to expose the urinary meatus 30, and inserting a female urethral catheter 31 into the urinary meatus 30.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:
1. A method of inserting a female urethral catheter, comprising:
   inserting a paddle of a female urethral catheterization assist device in a closed configuration to engage with a labia minora and majora;
   the female urethral catheterization assist device comprising:
   a pair of lateral arms comprising a first lateral arm and a second lateral arm, each lateral arm having a handle at a proximal end;
   a pivot interconnecting the pair of lateral arms, the pivot disposed intermediate the proximal end and a distal end;
   the pivot and the pair of lateral arms enabling free rotation of the handles of the pair of lateral arms towards each other and away from each other;
   the handle comprising an aperture adapted to receive a finger therethrough;
   the distal end of each lateral arm comprising a pair of curved lateral sides;
   wherein the pair of curved lateral sides consists of an interior lateral side and an exterior lateral side;
   the exterior lateral side curving outwardly from the lateral arm and away from the interior lateral side;
   the interior lateral side curving inwardly from the lateral arm and towards an opposing lateral arm;
   the paddle disposed on the interior lateral side, forming a flush surface therewith;
   the paddle defining a base in contact with the interior lateral side of the lateral arm;
   the paddle being of an arcuate shape, wherein a singular apex of the arcuate shape extends inwardly from the lateral arm;
   the arcuate shape consisting of a rounded body defining the singular apex;
   wherein the singular apex of the first lateral arm and the singular apex of the second lateral arm contact each other in the closed configuration;
   the paddle extending linearly upward entirely from the base of the paddle to a top edge thereof;
   opening the female urethral catheterization assist device to an open configuration to expose the urinary meatus; and
   inserting a female urethral catheter into the urinary meatus.

* * * * *